(12) United States Patent
Huang et al.

(10) Patent No.: US 12,422,373 B2
(45) Date of Patent: Sep. 23, 2025

(54) SYSTEM AND METHOD FOR ELECTROMAGNETIC MONITORING OF ACTIVE CRACKS IN CONCRETE DAM

(71) Applicant: Tsinghua University, Beijing (CN)

(72) Inventors: Songling Huang, Beijing (CN); Lisha Peng, Beijing (CN); Xinjie Yu, Beijing (CN); Jinghua Zhang, Beijing (CN); Shisong Li, Beijing (CN); Shuzhi Wen, Beijing (CN)

(73) Assignee: Tsinghua University, Beijing (CN)

( * ) Notice: Subject to any disclaimer, the term of this patent is extended or adjusted under 35 U.S.C. 154(b) by 275 days.

(21) Appl. No.: 18/329,804

(22) Filed: Jun. 6, 2023

(65) Prior Publication Data

US 2024/0219311 A1 Jul. 4, 2024

(30) Foreign Application Priority Data

Dec. 30, 2022 (CN) .......................... 202211735567.4

(51) Int. Cl.
*G01N 21/88* (2006.01)
*G01N 21/93* (2006.01)
*G01N 33/38* (2006.01)

(52) U.S. Cl.
CPC ......... *G01N 21/8851* (2013.01); *G01N 21/93* (2013.01); *G01N 33/383* (2013.01); *G01N 2021/8861* (2013.01); *G01N 2021/8877* (2013.01); *G01N 2201/12723* (2013.01)

(58) Field of Classification Search
CPC .. G01N 21/8851; G01N 21/93; G01N 33/383; G01N 2021/8861; G01N 2021/8877; G01N 2201/12723; G01N 27/83
See application file for complete search history.

(56) References Cited

U.S. PATENT DOCUMENTS

| | | | | |
|---|---|---|---|---|
| 4,480,480 A | * | 11/1984 | Scott | G01M 5/0016 702/41 |
| 2004/0153270 A1 | * | 8/2004 | Yamashita | G01N 33/383 702/81 |
| 2018/0238820 A1 | * | 8/2018 | Ghods | G01N 27/026 |
| 2019/0178850 A1 | * | 6/2019 | Su | G01N 29/225 |
| 2021/0063336 A1 | * | 3/2021 | Ghods | B28C 5/422 |
| 2021/0364459 A1 | * | 11/2021 | Minotani | G01N 27/9046 |

\* cited by examiner

*Primary Examiner* — Sang H Nguyen
(74) *Attorney, Agent, or Firm* — Osha Bergman Watanabe & Burton LLP

(57) ABSTRACT

The disclosure provides a system for electromagnetic monitoring of active cracks in a concrete dam. The system includes at least four electromagnetic signal acquisition devices and a main control module. Each electromagnetic signal acquisition device includes: an electromagnetic monitoring sensor, an electromagnetic signal acquisition module, a power supply module and a first wireless communication module, for collecting and extracting electromagnetic radiation signals generated by the active cracks in the concrete dam. The main control module includes: a second wireless communication module, a CPU, a data storage unit and a data display unit, for processing the electromagnetic radiation signals received by the second wireless communication module, positioning locations of the active cracks and quantifying sizes of the active cracks.

15 Claims, 3 Drawing Sheets

SYSTEM AND METHOD FOR ELECTROMAGNETIC MONITORING OF ACTIVE CRACKS IN CONCRETE DAM

CROSS-REFERENCE TO RELATED APPLICATION

This application claims priority to Chinese Patent Application No. 2022117355674, filed on Dec. 30, 2022, the entire content of which is incorporated by reference herein.

TECHNICAL FIELD

The disclosure relates to the field of online electromagnetic monitoring technology, in particular to a system and a method for electromagnetic monitoring of active cracks in a concrete dam.

BACKGROUND

Concrete dams, as large concrete structures, are important infrastructures for a hydroelectric power station that play a key role in many aspects such as irrigation, shipping and power generation. Meanwhile, due to the inherent characteristics of concrete materials, tiny cracks are inevitably caused during casting, and the tensile strength is much less than the compressive strength. After the concrete dams are put into operation, due to continuous changes in load-bearing, these tiny cracks are prone to develop and form active cracks, which may cause serious threats to the safety and stability of the dams. Therefore, monitoring active cracks in the concrete dam is of great importance.

SUMMARY

According to a first aspect of the disclosure, a system for electromagnetic monitoring of active cracks in a concrete dam is provided. The system includes at least four electromagnetic signal acquisition devices and a main control module. Each electromagnetic signal acquisition device includes: an electromagnetic monitoring sensor, an electromagnetic signal acquisition module, a power supply module and a first wireless communication module, for collecting and extracting electromagnetic radiation signals generated by the active cracks in the concrete dam. The main control module includes: a second wireless communication module, a CPU, a data storage unit and a data display unit, for processing the electromagnetic radiation signals received by the second wireless communication module, positioning locations of the active cracks and quantifying sizes of the active cracks.

According to a second aspect of the disclosure, a method for electromagnetic monitoring of active cracks in a concrete dam is provided. The method includes: selecting areas to be monitored based on a distribution pattern of the active cracks, arranging at least four electromagnetic signal acquisition devices uniformly on a concrete dam surface, and recording spatial locations of the electromagnetic signal acquisition devices; obtaining by an electromagnetic monitoring sensor, three-axis magnetic field components in a spatial electromagnetic radiation field of a sampling point in the selected areas; in response to filtering interference data caused by spatial electromagnetic radiation noises out of the three-axis magnetic field components, obtaining by an amplifier filter circuit and a data acquisition processor, electromagnetic radiation signals generated by the active cracks; sending the electromagnetic radiation signals to a main control module via wireless communication modules; obtaining by a central processing unit (CPU), a time of sending each electromagnetic radiation signal to the main control module, a amplitude, a frequency and a duration of each electromagnetic radiation signal; positioning a spatial location of an active crack by obtaining arrival time differences and amplitudes of electromagnetic radiation signals received by the main control module from 4 electromagnetic signal acquisition devices based on electromagnetic radiation signal propagation law and signal attenuation law; and determining a size of the active crack by comparing an amplitude, a frequency and a duration of each electromagnetic radiation signal from 4 electromagnetic signal acquisition devices based on a correspondence between electromagnetic radiation signal characteristics and active crack characteristics.

Additional aspects and advantages of the disclosure may be given in part in the following description, and part of the disclosure may become apparent from the following description, or learned from the practice of the disclosure.

BRIEF DESCRIPTION OF THE DRAWINGS

The above and/or additional aspects and advantages of the disclosure may become apparent and easily understood from the following description of the embodiments in combination with the accompanying drawings.

DETAILED DESCRIPTION

It is to be noted that the embodiments and the features in the embodiments of the disclosure can be combined with each other without conflict. The disclosure may be described in detail below with reference to the accompanying drawings and in combination with the embodiments.

In order to enable those skilled in the art to better understand the scheme of the disclosure, the technical solutions in the embodiments of the disclosure may be clearly and completely described below in combination with the accompanying drawings in the embodiments of the disclosure. The described embodiments are only a part of the embodiments of the disclosure, and not all of the embodiments of the disclosure. Based on the embodiments in the disclosure, all other embodiments obtained by those skilled in the art without inventive works shall fall within the scope of protection of the disclosure.

In the related art, there is no mature method for monitoring active cracks in a large-scale concrete dam. The manual inspection method is costly and labor-intensive, which can only evaluate crack defects periodically, but cannot determine the state of crack defects in real time. The method with infrared detection and image recognition can only identify cracks on the dam surface, but cannot detect internal defects in the dams. The acoustic emission method requires high signal-to-noise ratio for vibration signals in the environment, and strong vibration interference around the concrete dam makes it difficult to realize the monitoring of active cracks. The ultrasonic method is limited by the heterogeneous property of the concrete material, pores in the concrete material and other factors, which makes it difficult to apply the method to monitoring active cracks in the concrete dam.

In order to address the above problem in the related art, the embodiments of the disclosure provide a system and a method for electromagnetic monitoring of active cracks in a concrete dam, which are described below with reference to the accompanying drawings.

Figure 1:
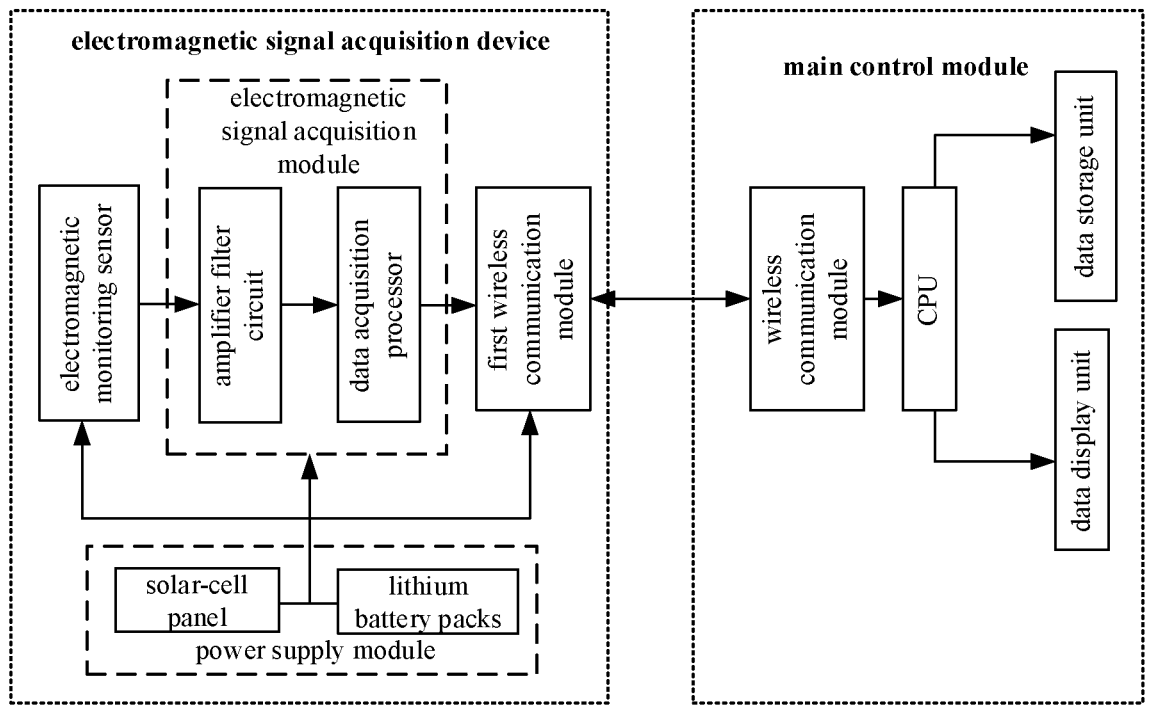
FIG. 1 is a structural diagram of a system for electromagnetic monitoring of active cracks in a concrete dam according to an embodiment of the disclosure.

FIG. 1 is a structural diagram of a system for electromagnetic monitoring of active cracks in a concrete dam according to an embodiment of the disclosure.

As shown in FIG. 1, the system includes: at least four electromagnetic signal acquisition devices and a main control module.

The electromagnetic signal acquisition device includes: an electromagnetic monitoring sensor, an electromagnetic signal acquisition module, a power supply module and a first wireless communication module, for collecting and extracting electromagnetic radiation signals generated by the active cracks in the concrete dam.

The main control module includes: a second wireless communication module, a central processing unit (CPU), a data storage unit and a data display unit, for processing the electromagnetic radiation signals received by the second wireless communication module, positioning locations of the active cracks and quantifying sizes of the active cracks.

Figure 2:
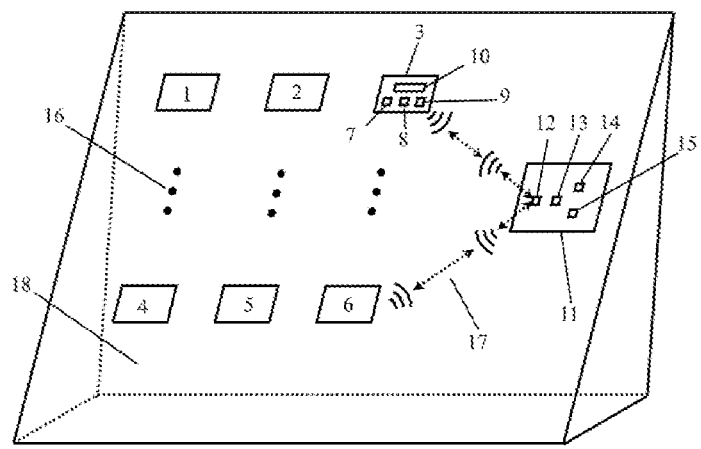
FIG. 2 is a spatial arrangement diagram of a system for electromagnetic monitoring of active cracks in a concrete dam according to an embodiment of the disclosure.

As shown in FIG. 2, it is a spatial arrangement diagram of a system for electromagnetic monitoring of active cracks in a concrete dam according to an embodiment of the disclosure. The system includes: a plurality of electromagnetic signal acquisition devices 1-6, and a main control module 11. Each electromagnetic signal acquisition device includes an electromagnetic monitoring sensor 7, an electromagnetic signal acquisition module 8, a first wireless communication module 9, and a power supply module 10. The main control module 11 includes a second wireless communication module 12, a CPU 13, a data storage unit 14, and a data display unit 15. The reference number 16 indicates that the number of electromagnetic signal acquisition devices is not limited to 6, and can be any number not less than 4, depending on the size of the monitoring area and the interval arranged between the electromagnetic signal acquisition devices.

The reference number 17 indicates that any electromagnetic signal acquisition device is communicated with the main control module in a wireless manner. In an example, any electromagnetic signal acquisition device is communicated with the main control module via the first and second wireless communication modules. The reference number 18 indicates the area to be monitored for active cracks on the dam body of the concrete dam. Each electromagnetic signal acquisition device includes an electromagnetic monitoring sensor, an electromagnetic signal acquisition module, a power supply module and a first wireless communication module. The internal structure of one of the electromagnetic signal acquisition devices (marked by the reference number 3) is shown in FIG. 2. The electromagnetic signal acquisition devices 1-6 and 16 are arranged at equal intervals on the surface of the area 18. The electromagnetic signal acquisition devices are arranged at a horizontal interval being less than 5 m and a longitudinal interval being less than 5 m on the concrete dam surface, for collecting and extracting electromagnetic radiation signals generated by the active cracks in the concrete dam. The power supply module 10 in the electromagnetic signal acquisition device 3 is used for supplying power to the electromagnetic monitoring sensor 7, the electromagnetic signal acquisition module 8 and the first wireless communication module 9. The first wireless communication module 9 carried in the electromagnetic signal acquisition device is connected to the second wireless communication module 12 carried in the main control module, for supporting communication between the electromagnetic signal acquisition module 8 and the main control module 11. The main control module 11 is configured to store, analyze and display the received electromagnetic radiation signals, position the locations of the active cracks and quantify the sizes of the active cracks.

In an embodiment of the disclosure, the electromagnetic monitoring sensor is an acquisition unit of spatial three-axis magnetic field signals, with a signal sampling rate being greater than 10 MHZ.

In an embodiment of the disclosure, the electromagnetic signal acquisition module includes an amplifier filter circuit and a data acquisition processor that are connected to the electromagnetic monitoring sensor, for filtering out power frequency electromagnetic noises and other electromagnetic interference noises, and a time length of the extracted electromagnetic radiation signal from a single active crack is greater than 2 ms.

In an embodiment of the disclosure, the power supply module is configured to supply power using a combination of lithium battery packs with high energy density and solar-cell panels. The solar panels are used to supply power when the light is sufficient, and the lithium battery packs are used to supply power when the light is insufficient. In detail, in this embodiment of the disclosure, a high-capacity lithium iron phosphate battery with 12V output produced by Contemporary Amperex Technology Co., Ltd. is used.

In an embodiment of the disclosure, the first and second wireless communication modules support ultra-wideband communication between the electromagnetic signal acquisition module and the main control module, and the first and second wireless communication modules are connected to the electromagnetic signal acquisition module and the CPU respectively, as shown in FIG. 1.

In an embodiment of the disclosure, the CPU receives information transmitted by the second wireless communication module and performs feature extraction analysis and judgment on the electromagnetic radiation signals collected by the electromagnetic signal acquisition module, to position the locations of the active cracks and quantify the sizes of the active cracks.

In an embodiment of the disclosure, the data storage unit is connected to the CPU for storing the electromagnetic radiation signal waveform data acquired by the CPU and storing the locations and the sizes of the active cracks acquired by the CPU.

In an embodiment of the disclosure, the data display unit is connected to the CPU for displaying time-frequency domain characteristics of the electromagnetic radiation signals, the sizes of the active cracks and an overall distribution of the active cracks.

It may be understood that the data acquisition processor used in this embodiment of the disclosure is STM32F7 series of very high-performance micro controller unit (MCU) produced by STMicroelectronics. The data storage unit is a high-speed 128G memory card produced by SanDisk. The electromagnetic monitoring sensor is a three-axis magnetic field sensor produced by Honeywell. Those skilled in the art can choose the device according to the actual situation, which is not limited herein.

The system for electromagnetic monitoring of active cracks in a concrete dam according to the embodiments of the disclosure solves the problem that it is difficult to monitor the active cracks in the concrete dam. The method for identifying the active cracks in the disclosure is simple with a fast identifying speed and a good real-time performance. Meanwhile, the system has a low power consumption.

Figure 3:
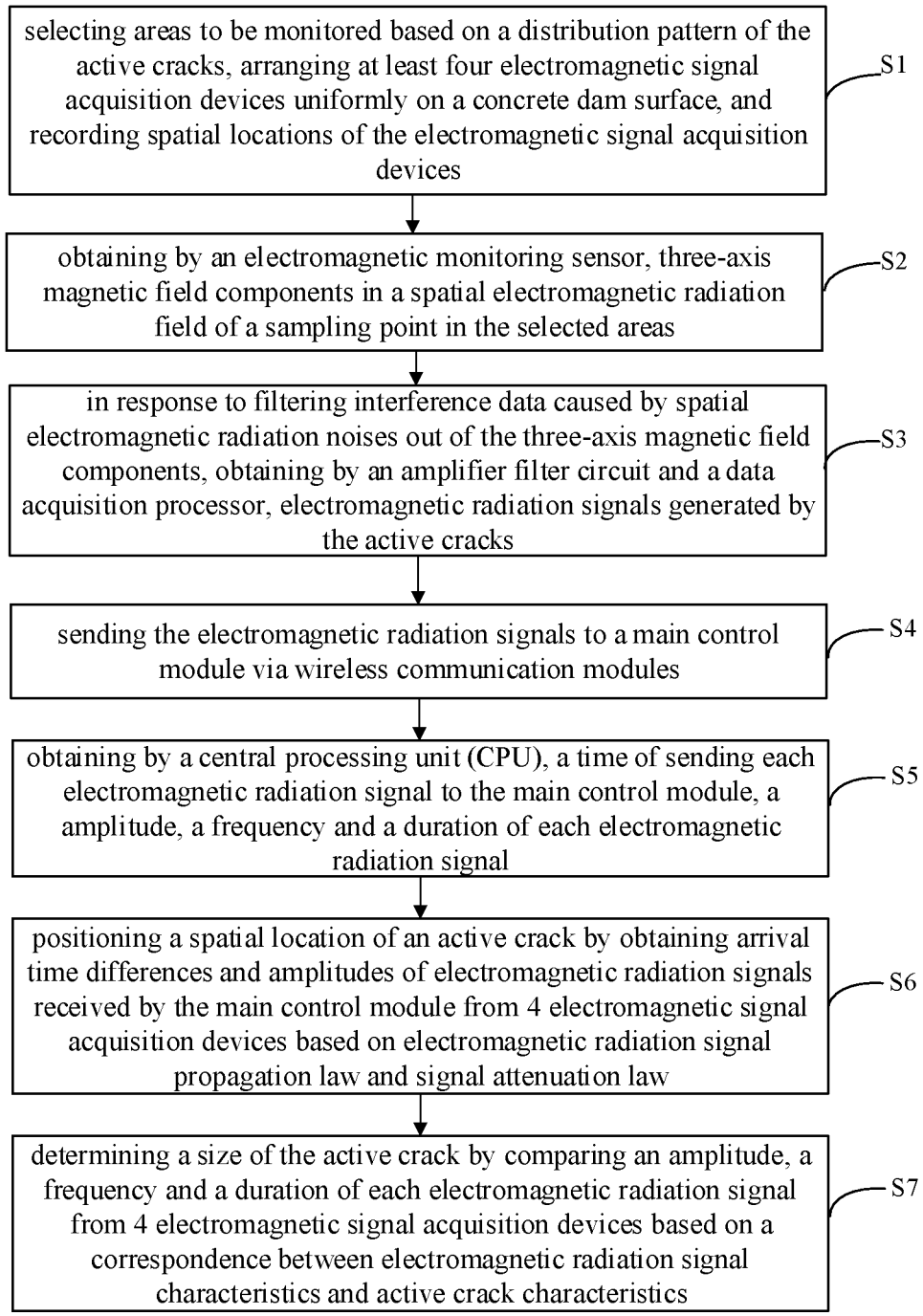
FIG. 3 is a flowchart of a method for electromagnetic monitoring of active cracks in a concrete dam according to an embodiment of the disclosure.

The method for electromagnetic monitoring of active cracks in a concrete dam according to the embodiments of the disclosure is described below. The method is performed by the above-described system according to the embodiments of the disclosure. As shown in FIG. 3, the method further includes the following steps.

At S1, areas to be monitored are selected based on a distribution pattern of the active cracks in a concrete dam, a plurality of electromagnetic signal acquisition devices are arranged uniformly on a concrete dam surface, and distribution locations of the electromagnetic signal acquisition devices are recorded.

At S2, three-axis magnetic field components in a spatial electromagnetic radiation field of a sampling point in the selected areas are obtained by the electromagnetic monitoring sensor.

At S3, electromagnetic radiation signals generated by the active cracks are obtained by an amplifier filter circuit and a data acquisition processor, after filtering interference data caused by spatial electromagnetic radiation noises out of the three-axis magnetic field components. That is, the interference data in three-axis magnetic field components are removed to obtain the electromagnetic radiation signals.

At S4, the electromagnetic radiation signals generated by the active cracks are sent to a main control module via wireless communication modules.

At S5, a time of sending the electromagnetic radiation signals to the main control module, a amplitude, a frequency and a duration of each electromagnetic radiation signal are obtained by a central processing unit (CPU).

At S6, a location of an active crack is positioned by obtaining arrival time differences and amplitudes of electromagnetic radiation signals received by the main control module from 4 electromagnetic signal acquisition devices based on electromagnetic radiation signal propagation law and signal attenuation law.

In the embodiments of the disclosure, a number of electromagnetic signal acquisition devices are more than 4. When a location of an active crack is positioned, in an ideal/theoretical situation, the 4 electromagnetic signal acquisition devices are randomly selected from all the electromagnetic signal acquisition devices. However, in the actual situation, the electromagnetic radiation signals may attenuate with the increase of distance away from the active crack. In order to accurately determine a location of an active crack, the received electromagnetic radiation signals are ranked based on the intensity and amplitude value, so as to determine 4 electromagnetic signal acquisition devices corresponding to the top 4 electromagnetic radiation signals. As such, the selected 4 electromagnetic signal acquisition devices are closer to the location of the active crack and it is easier and accurate to position the location of the active crack.

At S7, a size of the active crack is determined by comparing an amplitude, a frequency and a duration of each electromagnetic radiation signal received by the main control module from 4 electromagnetic signal acquisition devices based on a correspondence between electromagnetic radiation signal characteristics and active crack characteristics.

Figure 4:
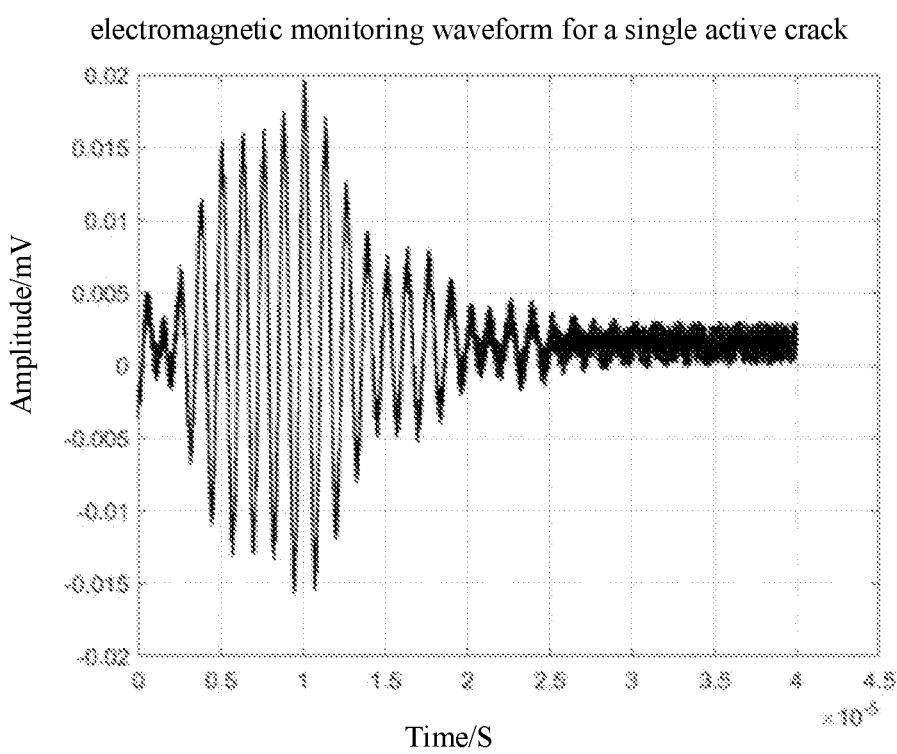
FIG. 4 is a waveform diagram of a single electromagnetic radiation signal generated by the active cracks according to an embodiment of the disclosure.

In an embodiment of the disclosure, the electromagnetic radiation signal waveform generated by the active cracks in a concrete dam is shown in FIG. 4.

In an embodiment of the disclosure, the selected areas to be monitored are the areas prone to form cracks during daily inspections. In an example, the selected areas includes areas with a high load bearing ratio, areas prone to form a crack during daily inspection, and areas with minor cracks where severe cracking has not yet occurred.

In an embodiment of the disclosure, the three-axis magnetic field components in the spatial electromagnetic radiation field of the collection point includes: x-y-z-axes magnetic field components collected by the electromagnetic monitoring sensor, in which the three axes are perpendicular to each other.

In an embodiment of the disclosure, filtering the interference data caused by the spatial electromagnetic radiation noises includes: in response to a frequency band of sampling signals obtained by the electromagnetic monitoring sensor being outside of a range between 10 kHz and 10 MHz, or the sampling signals being non-pulse attenuation signals, or being received by less than 4 electromagnetic signal acquisition devices, determining that the sampling signals are environmental interference noises, and filtering out the environmental interference noises.

In an embodiment of the disclosure, the electromagnetic radiation signal propagation law and the signal attenuation law include: a propagation rate of each electromagnetic radiation signal in the air is the speed of light, a propagation rate of each electromagnetic radiation signal in a concrete medium is related to a refractive index of electromagnetic waves in the concrete medium, and attenuation of the electromagnetic radiation signals is related to a signal frequency.

In an embodiment of the disclosure, comparing the arrival time differences and the amplitudes of the electromagnetic radiation signals includes:

determining based on the arrival time differences and the amplitudes, distances d1, d2, d3, d4 between each of the 4 electromagnetic signal acquisition devices and the active crack, determining the spatial locations (x1, y1, z1), (x2, y2, z2), (x3, y3, z3), and (x4, y4, z4) of the 4 electromagnetic signal acquisition devices, and determining a spatial location (x, y, z) of the active crack based on basic principles of spatial four-point localization, in which (x, y, z) satisfies the following equation:

$$\begin{bmatrix} 2(x_1 - x_2) & 2(y_1 - y_2) & 2(z_1 - z_2) \\ 2(x_1 - x_3) & 2(y_1 - y_3) & 2(z_1 - z_3) \\ 2(x_1 - x_4) & 2(y_1 - y_4) & 2(z_1 - z_4) \end{bmatrix} \begin{bmatrix} x \\ y \\ z \end{bmatrix} = \begin{bmatrix} d_2^2 - d_1^2 - x_2^2 + x_1^2 - y_2^2 + y_1^2 - z_2^2 + z_1^2 \\ d_3^2 - d_1^2 - x_3^2 + x_1^2 - y_3^2 + y_1^2 - z_3^2 + z_1^2 \\ d_4^2 - d_1^2 - x_4^2 + x_1^2 - y_4^2 + y_1^2 - z_4^2 + z_1^2 \end{bmatrix}$$

In detail, the distances d1, d2, d3 and d4 between the active crack and the 4 electromagnetic signal acquisition devices are obtained, that is, d1=2.45 m, d2=4.58 m, d3=4.58 m, d4-6 m, and the spatial locations (0, 0, 0) (0, 5 m, 0) (5 m, 0, 0) (5 m, 5 m, 0) of the 4 electromagnetic signal acquisition devices are determined. The spatial location of the active crack is determined by the basic principle of spatial four-point positioning as (1 m, 1 m, −2 m).

In an embodiment of the disclosure, the correspondence between the electromagnetic radiation signal characteristics and the active crack characteristics includes: the amplitude and the frequency of the electromagnetic radiation signals are related to a width of the active crack, and the duration of the electromagnetic radiation signals is related to a length of the active crack.

The method for monitoring electromagnetic of active cracks in the concrete dam according to the embodiments of the disclosure can realize the monitoring of active cracks in the concrete dam by using the electromagnetic radiation signals generated by the active cracks, while positioning the specific locations of the active cracks on the dam body and quantifying the sizes of the active cracks. The monitoring system can monitor the active cracks inside the concrete dam, with a wider monitoring range and higher reliability. The method has a simple solution and a good real-time performance. The system has a low power consumption.

Any process or method description in the flowchart or otherwise described herein may be understood to represent a module, fragment or part of code including one or more executable instructions for implementing the steps of a particular logical function or process, and the scope of the embodiments of the present disclosure includes additional implementations where the functions may be performed in in an order shown or discussed, or includes implementations where the functions may be performed in a basically simultaneous manner or in reverse order according to the involved functions, which may be understood by those skilled in the art.

It should be understood that various parts of the disclosure may be implemented in hardware, software, firmware or their combination. In the above described embodiments, a plurality of steps or methods may be implemented with software or firmware stored in memory and executed by a suitable instruction execution system. For example, if they are implemented in hardware, as in another embodiment, it can be implemented by any of the following technologies known in the art or their combination: discrete logic circuits with logic gate circuits for realizing logic function of data signals, application specific integrated circuits with appropriate combined logic gate circuits, a programmable gate array (PGA), a field programmable gate array (FPGA), etc.

The terms "module," "circuit," or "unit," may include memory (shared, dedicated, or group) that stores code or instructions that can be executed by one or more processors. A module may include one or more circuits with or without stored code or instructions. The module or circuit may include one or more components that are directly or indirectly connected. These components may or may not be physically attached to, or located adjacent to, one another. A unit or module may be implemented purely by software, purely by hardware, or by a combination of hardware and software. In a pure software implementation, for example, the unit or module may include functionally related code blocks or software components that are directly or indirectly linked together, so as to perform a particular function.

In addition, each functional unit in each embodiment of the disclosure can be integrated into one processing module, each unit can exist separately, or two or more units can be integrated into one module. The above integrated modules can be realized in the form of hardware or software function modules. If the integrated module is realized in the form of software function module and sold or used as an independent product, it can also be stored in a computer-readable storage medium. The storage medium can be a read only memory, a magnetic disk or an optical disc.

In the description of the disclosure, the reference terms "an embodiment", "some embodiments", "example", "specific example", and "some examples" and the like are intended to describe specific features, structures, materials, or characteristics described in combination with the embodiments or examples are included in at least one embodiment or example of the disclosure. In this disclosure, the schematic expressions of the above terms do not have to be directed to the same embodiments or examples. Moreover, the specific features, structures, materials, or characteristics described may be combined in a suitable manner in any one or more embodiments or examples. In addition, without contradicting each other, those skilled in the art may combine different embodiments or examples described in this disclosure and features of different embodiments or examples.

It should be noted that, the terms "first" and "second" are only for describing purposes and are not to be construed as indicating or implying relative importance or implicitly indicating the number of technical features indicated. Thus, features limiting "first" and "second" may explicitly or implicitly include at least one of the features. In the description of the disclosure, the wording "a plurality of" means at least two, for example, two, three, unless otherwise expressly and specifically stated.

What is claimed is:

1. A method for electromagnetic monitoring of active cracks in a concrete dam, comprising:
   selecting areas to be monitored based on a distribution pattern of the active cracks, arranging at least four electromagnetic signal acquisition devices uniformly on a concrete dam surface, and recording spatial locations of the electromagnetic signal acquisition devices;
   obtaining by an electromagnetic monitoring sensor, three-axis magnetic field components in a spatial electromagnetic radiation field of a sampling point in the selected areas;
   in response to filtering interference data caused by spatial electromagnetic radiation noises out of the three-axis magnetic field components, obtaining by an amplifier filter circuit and a data acquisition processor, electromagnetic radiation signals generated by the active cracks;
   sending the electromagnetic radiation signals to a main control device via wireless communication devices;
   obtaining by a central processing unit (CPU), a time of sending each electromagnetic radiation signal to the main control device, an amplitude, a frequency and a duration of each electromagnetic radiation signal;
   positioning a spatial location of an active crack by obtaining arrival time differences and amplitudes of electromagnetic radiation signals received by the main control device from four electromagnetic signal acquisition devices based on electromagnetic radiation signal propagation law and signal attenuation law; and
   determining a size of the active crack by comparing an amplitude, a frequency and a duration of each electromagnetic radiation signal from four electromagnetic signal acquisition devices based on a correspondence between electromagnetic radiation signal characteristics and active crack characteristics.

2. The method of claim 1, wherein the selected areas comprise: areas with a high load bearing ratio, areas prone to form a crack during daily inspection, and areas with minor cracks where severe cracking has not yet occurred.

3. The method of claim 1, wherein the three-axis magnetic field components comprise: x-y-z-axes magnetic field components collected by the electromagnetic monitoring sensor, wherein the three axes are perpendicular to each other.

4. The method of claim 3, wherein the electromagnetic monitoring sensor is an acquisition unit spatial of three-axis magnetic field signals, with a signal sampling rate being greater than 10 MHz.

5. The method of claim 3, wherein the electromagnetic signal acquisition device comprises an amplifier filter circuit and a data acquisition processor that are connected to the electromagnetic monitoring sensor, for filtering out power frequency electromagnetic noises and other electromagnetic interference noises, and a time length of the extracted electromagnetic radiation signal from a single active crack is greater than 2 ms.

6. The method of claim 5, wherein power is supplied to the electromagnetic monitoring sensor, the electromagnetic signal acquisition device, and the first wireless communication device through the power supply device; and a combination of lithium battery packs with high energy density and solar-cell panels is used, wherein the solar panels are configured to supply power under a first light intensity, and the lithium battery packs are configured to supply power under a second light intensity.

7. The method of claim 6, wherein the first and second wireless communication devices are configured to support ultra-wideband communication between the electromagnetic signal acquisition device and the main control device, and the first and second wireless communication devices are connected to the electromagnetic signal acquisition device and the CPU respectively.

8. The method of claim 1, wherein filtering the interference data caused by the spatial electromagnetic radiation noises comprises:

in response to a frequency band of sampling signals obtained by the electromagnetic monitoring sensor being outside of a range between 10 kHz and 10 MHz, or the sampling signals being non-pulse attenuation signals, or being received by less than four electromagnetic signal acquisition devices, determining that the sampling signals are environmental interference noises, and filtering out the environmental interference noises.

9. The method of claim 1, wherein the electromagnetic radiation signal propagation law and the signal attenuation law comprise: a propagation rate of the electromagnetic radiation signals in the air is the speed of light, a propagation rate of each electromagnetic radiation signal in a concrete medium is related to a refractive index of electromagnetic waves in the concrete medium, and attenuation of the electromagnetic radiation signals is related to a signal frequency.

10. The method of claim 1, wherein comparing the arrival time differences and the amplitudes of the electromagnetic radiation signals comprises:

determining distances d1, d2, d3, d4 between each of the four electromagnetic signal acquisition devices and the active crack, determining the spatial locations (x1, y1, z1), (x2, y2, z2), (x3, y3, z3), and (x4, y4, z4) of the 4 electromagnetic signal acquisition devices, and determining the spatial location (x, y, z) of the active crack based on basic principles of spatial four-point localization, wherein (x, y, z) satisfies the following equation:

$$\begin{bmatrix} 2(x_1-x_2) & 2(y_1-y_2) & 2(z_1-z_2) \\ 2(x_1-x_3) & 2(y_1-y_3) & 2(z_1-z_3) \\ 2(x_1-x_4) & 2(y_1-y_4) & 2(z_1-z_4) \end{bmatrix} \begin{bmatrix} x \\ y \\ z \end{bmatrix} = \begin{bmatrix} d_2^2 - d_1^2 - x_2^2 + x_1^2 - y_2^2 + y_1^2 - z_2^2 + z_1^2 \\ d_3^2 - d_1^2 - x_3^2 + x_1^2 - y_3^2 + y_1^2 - z_3^2 + z_1^2 \\ d_4^2 - d_1^2 - x_4^2 + x_1^2 - y_4^2 + y_1^2 - z_4^2 + z_1^2 \end{bmatrix}.$$

11. The method of claim 1, wherein the correspondence between the electromagnetic radiation signal characteristics and the active crack characteristics comprises: the amplitude and the frequency of the electromagnetic radiation signals are related to a width of the active crack, and the duration of the electromagnetic radiation signals is related to a length of the active crack.

12. The method of claim 1, wherein the plurality of electromagnetic signal acquisition devices are arranged at equal intervals on a concrete dam surface, the electromagnetic signal acquisition devices are arranged at a horizontal interval being less than 5 m and at a longitudinal interval being less than 5 m on the concrete dam surface.

13. The method of claim 1, wherein the CPU is configured to receive electromagnetic radiation signals and perform feature extraction analysis on the received electromagnetic radiation signals, to position the spatial locations of the active cracks and quantify the sizes of the active cracks.

14. The method of claim 1, wherein the data storage unit connected to the CPU stores waveform data of the electromagnetic radiation signals, and the spatial locations and the sizes of the active cracks acquired by the CPU.

15. The method of claim 1, wherein the data display unit connected to the CPU displays time-frequency domain characteristics of the electromagnetic radiation signals, the sizes of the active cracks and an overall distribution of the active cracks.

* * * * *